(12) United States Patent
Capcelea et al.

(10) Patent No.: US 9,008,796 B2
(45) Date of Patent: *Apr. 14, 2015

(54) DRUG RETAINING SURFACE FEATURES IN AN IMPLANTABLE MEDICAL DEVICE

(71) Applicant: Cochlear Limited, Macquarie University, NSW (AU)

(72) Inventors: Edmond Capcelea, Sydney (AU); Fysh Dadd, Lane Cove (AU); Kristien J. M. Verhoeven, Zoersel (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,202

(22) Filed: Aug. 5, 2013

(65) Prior Publication Data

US 2014/0100514 A1  Apr. 10, 2014

Related U.S. Application Data

(63) Continuation of application No. 13/107,009, filed on May 13, 2011, now Pat. No. 8,504,169.

(51) Int. Cl.

| | |
|---|---|
| *A61N 1/00* | (2006.01) |
| *A61N 1/36* | (2006.01) |
| *A61N 1/05* | (2006.01) |
| *A61N 1/375* | (2006.01) |
| *A61M 37/00* | (2006.01) |
| *A61F 11/00* | (2006.01) |

(52) U.S. Cl.
CPC .......... *A61N 1/36032* (2013.01); *A61N 1/0541* (2013.01); *A61N 1/375* (2013.01); *A61M 37/00* (2013.01); *A61F 11/00* (2013.01)

(58) Field of Classification Search
USPC .......................................... 607/116
See application file for complete search history.

(56) References Cited

U.S. PATENT DOCUMENTS

| | | | |
|---|---|---|---|
| 7,949,412 B1 * | 5/2011 | Harrison et al. | 607/137 |
| 8,190,271 B2 * | 5/2012 | Overstreet et al. | 607/137 |
| 2005/0165452 A1 | 7/2005 | Sigg et al. | |
| 2006/0287689 A1 | 12/2006 | Debruyne et al. | |
| 2007/0088335 A1 * | 4/2007 | Jolly | 604/891.1 |
| 2009/0054961 A1 * | 2/2009 | Borgaonkar et al. | 607/116 |
| 2009/0203953 A1 | 8/2009 | Lamoureaux et al. | |
| 2010/0030130 A1 | 2/2010 | Parker et al. | |
| 2010/0239635 A1 | 9/2010 | McClain et al. | |

(Continued)

FOREIGN PATENT DOCUMENTS

| | | |
|---|---|---|
| WO | 2004050056 A1 | 6/2004 |
| WO | 2007148231 A2 | 12/2007 |

(Continued)

OTHER PUBLICATIONS

International Search Report and Written Opinion for International Application No. PCT/IB2012/052336 mailed Nov. 16, 2012 (18 pages).

*Primary Examiner* — Robert N Wieland

(57) ABSTRACT

An implantable component of a medical device, comprising a polymeric surface. The component includes one or more macro-surface features at the polymeric surface having a configuration that, following application of a liquid drug to the surface retains a quantity of the liquid drug adjacent the surface.

20 Claims, 10 Drawing Sheets

(56) References Cited

U.S. PATENT DOCUMENTS

2011/0150972 A1    6/2011  Strickler et al.
2013/0144370 A1*   6/2013  Debruyne et al. ............ 607/137

FOREIGN PATENT DOCUMENTS

WO    2008045242  A2    4/2008
WO    2010025517  A1    3/2010

* cited by examiner

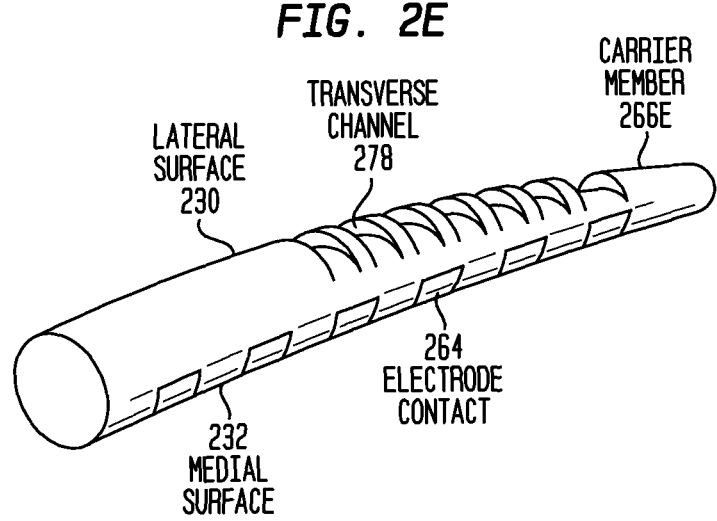
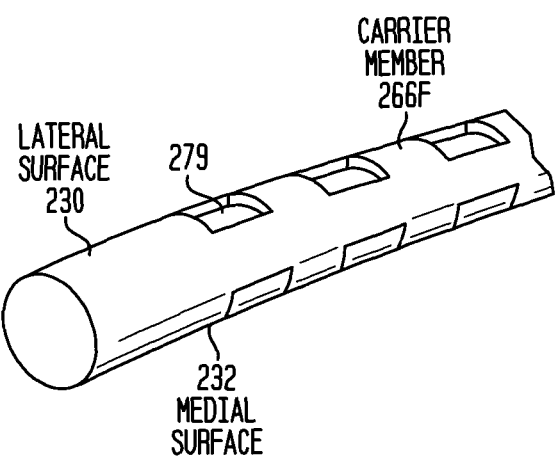

DRUG RETAINING SURFACE FEATURES IN AN IMPLANTABLE MEDICAL DEVICE

CROSS-REFERENCE TO RELATED APPLICATIONS

This application is a Continuation application of U.S. patent application Ser. No. 13/107,009 filed on May 13, 2011, issued on Aug. 6, 2013, now U.S. Pat. No. 8,504,169, which is hereby incorporated by reference herein.

BACKGROUND

1. Field of the Invention

The present invention relates generally to implantable medical devices, and more particularly, to drug retaining surface features in an implantable medical device 2. Related Art Medical devices having one or more implantable components, generally referred to as implantable medical devices, have provided a wide range of therapeutic benefits to patients over recent decades. Implantable medical devices often include one or more instruments, apparatus, sensors, processors, controllers or other functional components that are permanently or temporarily implanted in a patient. The implanted components are used to, for example, diagnosis, monitor, or treat a disease or injury, or to modify the patient's anatomy or a physiological process. Many of these implantable components receive energy (i.e. power and/or data) from external components that are part of, or operate in conjunction with, the implantable component. Implantable hearing prostheses that treat the hearing loss of a prosthesis recipient are one particular type of implantable medical devices that are widely used today.

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an implantable hearing prosthesis that generates mechanical motion of the cochlea fluid. Some such hearing prosthesis, such as acoustic hearing aids, middle ear implants, etc., include one or more components implanted in the recipient, and are referred to herein as implantable hearing prosthesis.

SUMMARY

In one aspect of the present invention, an elongate implantable carrier member is provided. The carrier member comprises a plurality of electrode contacts disposed in the carrier member; and one or more macro-surface features in the carrier member having a configuration that, following application of a liquid drug to the carrier member, at least temporarily retain a quantity of the drug adjacent the carrier member surface.

In another aspect of the present invention, a method of delivering drugs to a recipient using an implantable component of medical comprises a plurality of macro-surface features having a configuration that at least temporarily retains a quantity of a liquid drug adjacent the surface of the component is provided. The method comprising: applying one or more liquid drugs to the component; and implanting the implantable component into the recipient.

In another aspect of the present invention, an implantable component of a medical device is provided. The implantable component comprises a polymeric surface; and one or more macro-surface features at the polymeric surface having a configuration that, following application of a liquid drug to the surface, at least temporarily retain a quantity of the liquid drug adjacent the surface.

In a still other aspect of the present invention, an implantable component of a medical device is provided. The implantable component comprises a polymeric surface; and one or more protrusions at the polymeric surface having a configuration that, following application of a liquid drug to the surface, at least temporarily retain a quantity of the liquid drug adjacent the surface.

BRIEF DESCRIPTION OF THE DRAWINGS

Embodiments of the present invention are described below with reference to the attached drawings, in which:

FIG. 2E is a perspective view of a carrier member having macro-surface features, in accordance with embodiments of the present invention;

FIG. 2F is a perspective view of a carrier member having macro-surface features, in accordance with embodiments of the present invention;

DETAILED DESCRIPTION

Aspects of the present invention are generally directed to the delivery of liquid bioactive substances or chemicals (collectively referred to as "drugs" herein) in conjunction with a component of implantable medical device. The component includes a polymeric surface, and a plurality of surface features at the surface. The features have a configuration (type, shape and/or size) that, following application of a liquid drug to the surface, at least temporarily retains a quantity of the drug adjacent the surface.

For ease of description, embodiments of the present invention will be primarily described with reference to surface features in an elongate carrier member of a cochlear implant. However, it would be appreciated that embodiments of the present invention may be implemented in a variety of implantable medical device components.

Figure 1A:
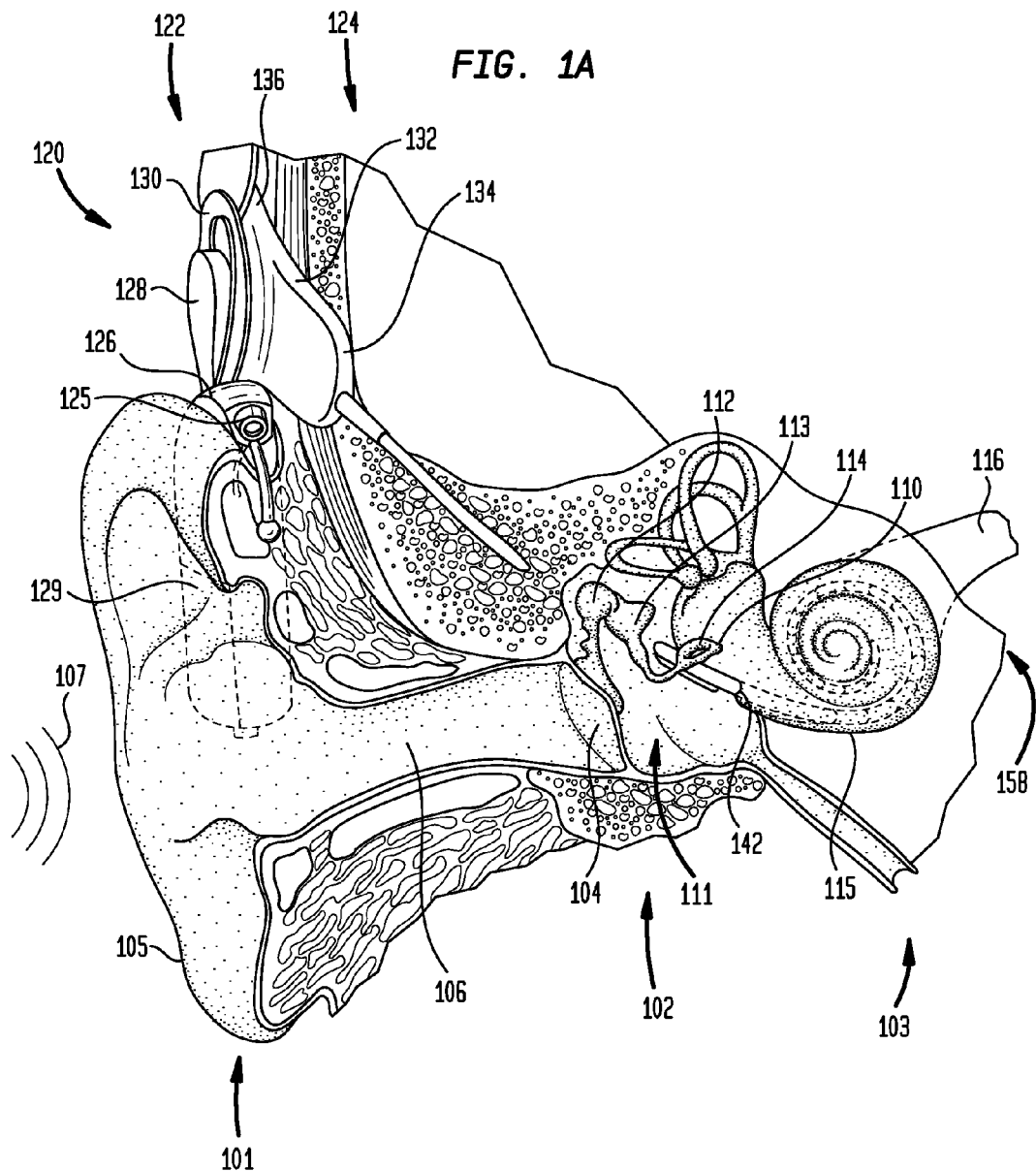
FIG. 1A is a perspective view of a cochlear implant in accordance with embodiments of the present invention, shown implanted in a recipient.

FIG. 1A is perspective view of an exemplary cochlear implant 120 in which embodiments of the present invention may implemented. In FIG. 1, cochlear implant 120 is shown implanted in a recipient. The relevant components of the recipient's outer ear 101, middle ear 102 and inner ear 103 are described next below, followed by a description of cochlear implant 120.

In a fully functional ear, outer ear 101 comprises an auricle 105 and an ear canal 106. An acoustic pressure or sound wave 107 is collected by auricle 105 and channeled into and through ear canal 106. Disposed across the distal end of ear canal 106 is a tympanic membrane 104 which vibrates in response to sound wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify sound wave 107, causing oval window 110 to articulate, or vibrate. Such vibration sets up waves of fluid motion within cochlea 115. Such fluid motion, in turn, activates hair cells (not shown) that line the inside of cochlea 115. Activation of the hair cells causes appropriate nerve impulses to be generated. The nerve impulses are transferred through the spiral ganglion cells and auditory nerve 116 to the brain (also not shown), where they are perceived as sound.

Cochlear implant 120 comprises external component assembly 122 which is directly or indirectly attached to the body of the recipient, and an internal component assembly 124 which is implanted in the recipient. External assembly 122 typically comprises one or more audio pickup devices for detecting sound such as microphone 125, a sound processor 126, a power source (not shown), and an external transmitter unit 128. External transmitter unit 128 comprises an external coil 130 of a transcutaneous energy transfer arrangement. Sound processor 126 processes the electrical signals generated by microphone 125 that is positioned, in the depicted embodiment, by auricle 105 of the recipient. Sound processor 126 generates coded signals, referred to herein as a stimulation data signals, which are provided to external transmitter unit 128 via a cable (not shown).

Internal assembly 124 comprises an internal receiver unit 132, a stimulator unit 134, and an elongate stimulating assembly 150 described further below with reference to FIG. 1B. Internal receiver unit 132 comprises an internal coil 136 of the transcutaneous energy transfer arrangement. Internal receiver unit 132 and stimulator unit 134 are hermetically sealed within a biocompatible housing. The internal coil receives power and stimulation data from external coil 130, as noted above. Stimulating assembly 150 has a proximal end connected to stimulator unit 134 and extends from stimulator unit 134 to cochlea 115. Stimulating assembly 150 is implanted into cochlea 115 via a cochleostomy 142.

In some cochlear implants, external coil 130 transmits electrical signals (that is, power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 105 of the recipient.

Figure 1B:
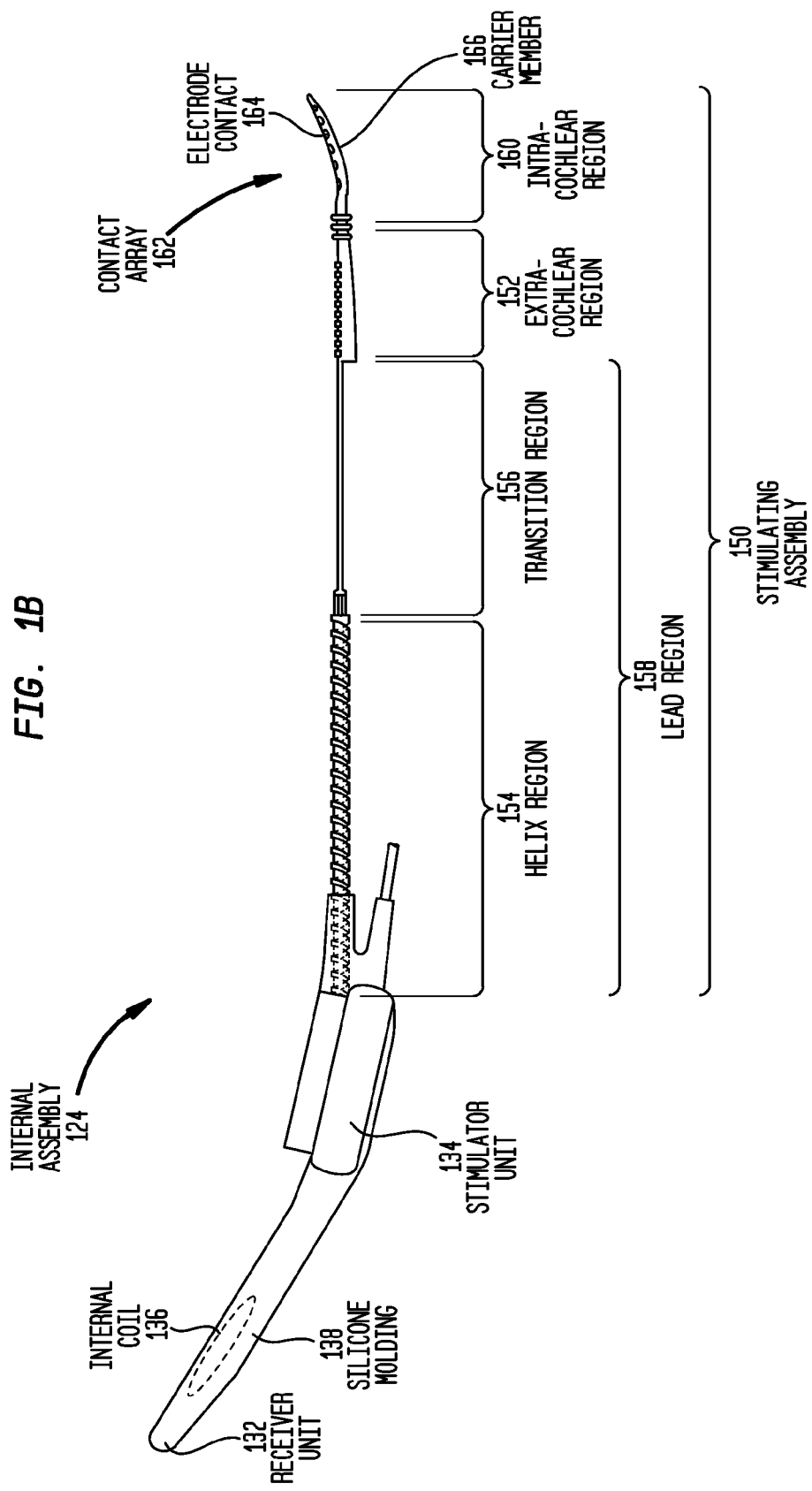
FIG. 1B is a side view of an embodiment of an implantable component of the cochlear implant illustrated in FIG. 1A.

FIG. 1B is a side view of an embodiment of internal assembly 124, introduced above with reference to FIG. 1A. As noted, internal assembly 124 comprises implantable receiver unit 132, stimulator unit 134, and stimulating assembly 150. Stimulating assembly 150 is configured to be implanted such that a portion of the stimulating assembly referred to as the intra-cochlear region 160 is positioned in cochlea 115 (FIG. 1) via, for example, cochleostomy 142 (FIG. 1). Stimulating assembly 150 further comprises an extra-cochlear region 152 that, when implanted, is positioned external to cochlea 115.

Intra-cochlear region 160 has a carrier member 166 that is formed of a biocompatible polymer, such as silicone. Carrier member 166 includes an array 162 of electrode contacts 164 configured to deliver stimulation to cochlea 115. Signals generated by stimulator unit 134 are applied by electrode contacts 164 to auditory nerve fibers 116 in cochlea 115, thereby stimulating auditory nerve 116 (FIG. 1). Stimulating assembly 150 also comprises a cable or lead region 158 which extends from stimulator unit 134 to extra-cochlear region 152 to physically and electrically connect intra-cochlear region 160 to stimulator unit 134 (via extra-cochlear region 152). As such, a proximal end of lead region 158 is connected to stimulator unit 134 while a distal end of lead region 158 is connected to extra-cochlear region 152 of stimulating assembly 318.

Lead region 158 is comprised of a helix region 154 connected to stimulator unit 134, and a transition region 156 connecting helix region 154 with extra-cochlear region 152. Helix region 154 provides protection against tensile stresses applied to stimulating assembly 150. Lead region 158 has a sufficient length to facilitate the implantation of stimulating assembly 150 in a variety of recipients.

There traditionally has been interest in delivering bioactive substances or chemicals (collectively "drug" herein) in conjunction with an implantable hearing prosthesis or other implantable medical device. The term "drug," as used herein, includes any bioactive substance now or later developed, including, but not limited to, pharmaceuticals and other chemical compounds intended to provide therapeutic benefits to, or other reactions in, a recipient, whether localized or distributed throughout the recipient, as well as well as solutions containing such substances. Bioactive substances may include, for example, steroids or other anti-inflammatory drugs to reduce inflammation at the implantation site. Another class of bioactive substances that may be included in the drug-delivery accessories are antibiotics to mitigate bacterial growth related to the implantation of the medical device. Additionally, as used herein, "liquid drug" includes drugs in liquid form, or a drug that is suspended in a liquid. As such, "liquid drug" includes any liquid solution that contains a drug.

In one conventional drug delivery approach, the implantable medical device is coated with a drug. In another conventional approach, a drug is integrated into a polymeric coating of the implantable medical device. These and other conventional approaches typically require the incorporation of the drug into the implantable medical device during the manufacturing process of the device. This introduces a number of difficult problems and challenges for the manufacturing and sterilization processes, particularly for complex implantable medical devices.

In other conventional drug delivery approaches, liquid drugs are contained in an external or implanted reservoir and are transferred to a target location in a patient. Such variations increase the complexity of the device, and may lead to failure or surgical complications.

Embodiments of the present invention are directed to another drug delivery method that avoids such manufacturing, sterilization, and complexity/failure concerns. Specifically, in embodiments of the present invention, an implantable component includes a polymeric surface, and a plurality of surface features at the surface. One or more liquid drugs are applied to the surface of the component immediately prior to implantation into the recipient, and the surface features have a configuration that temporarily retains a quantity of the liquid drug adjacent the surface of the component. As used herein, a surface feature is an indentation in, or protrusion from, the surface of an implantable component, such as a carrier member. As is known, a quantity of liquid will collect due to cohesive forces within the liquid, and the quantity is determined, in part, based on such cohesive forces. Indentations have a configuration (type, shape and/or size) such that when a liquid drug is applied to the carrier member, the liquid will collect within the indentation, and will be, at least temporarily, retained therein. Protrusions have a configuration (type, shape and/or size) such that when a liquid drug is applied to the carrier member, a quantity of the liquid will collect between adjacent protrusions, and will be, at least temporarily, retained there between.

The indentations or protrusions in accordance with embodiments of the present invention retain the liquid drug(s) "adjacent to" the surface of the component. That is, a quantity of drug within an indentation, or a quantity of drug retained between protrusions, is referred to as being adjacent to the surface of the component.

In certain embodiments of the present invention, the surface features are referred to as macro-surface features. In embodiments in which the macro-surface features are indentations in the surface of the carrier member, the indentations are referred to as being "macro" because each indentation generally has a volume of approximately at least 0.001 mm$^3$, or have a dimension (length, width, height) of approximately 100 μm. In certain embodiments in which the macro-surface features are protrusions from the surface of the carrier member, the protrusions have one more dimensions (length, width, height) that are at least 100 μm, or define a volume between adjacent protrusions that is at least 0.001 mm$^3$.

Because, as noted above, the liquid drug is applied to, and retained adjacent to the surface of the component, the drug is delivered to the recipient during, or immediately following implantation. Additionally, because the drug is applied after manufacture, the selection of the drug occurs at time of surgery, the drug does not need to withstand sterilization, and there is no additional component that adds complexity to the device.

Figure 2A:
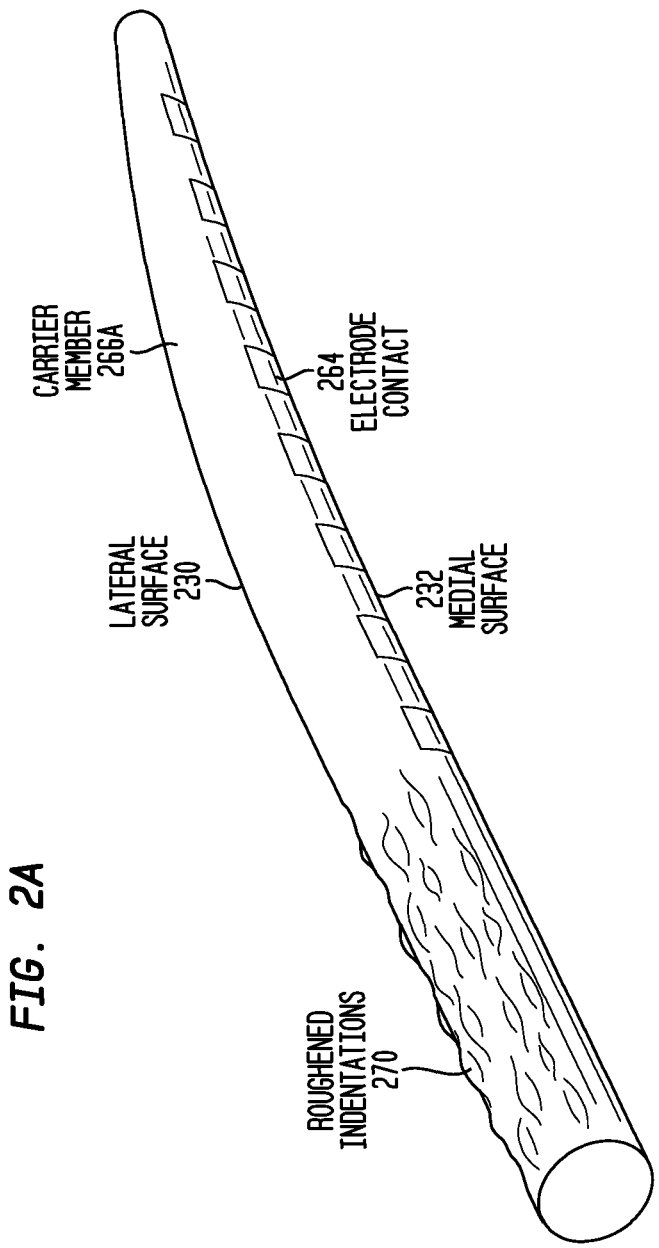
FIG. 2A is a perspective view of a carrier member having macro-surface features, in accordance with embodiments of the present invention.

FIG. 2A is a partial perspective view of a carrier member 266A including macro-surface features in accordance with embodiments of the present invention. When implanted in cochlea 115, the surface of carrier member 266A that faces the interior nerve cells of cochlea 115 is referred to herein as the medial surface 263. The opposing side of carrier member 266A faces the external wall and bony capsule (not shown) of cochlea 115 and is referred to herein as lateral surface 230. As such, the terms medial surface, medial direction, and the like, are generally used herein to refer to the surfaces, features and directions toward the center of cochlea 115, while the terms lateral surface, lateral direction, and the like, are generally used herein to refer to surfaces, features and directions toward the exterior of cochlea 115. The carrier member 266A is a component of a stimulating assembly and, as such, includes a plurality of electrode contacts 264 disposed therein. As shown, the electrode contacts 264 are disposed at or in medial surface 232.

In this illustrative embodiment, the macro-surface features including a plurality of indentations 270 in lateral surface 230 formed through a surface roughening procedure. Additionally, roughened indentations 270 are sized and/or shaped such that when a liquid drug is applied to carrier member 266A, a quantity of the drug will collect within the indentations. As such, the quantity will be, at least temporarily, retained adjacent the surface of carrier member 266A. In embodiment, the liquid drug is applied by dipping carrier member 266A into the liquid.

In the embodiments of FIG. 2A, indentations 270 are shown on lateral surface 230 of carrier member 266A. It would be appreciated that in certain embodiments indentations 270 may be on medial surface 232, or may be on the surface of carrier member 266A between the lateral and medial surfaces 230, 232.

Figure 2B:
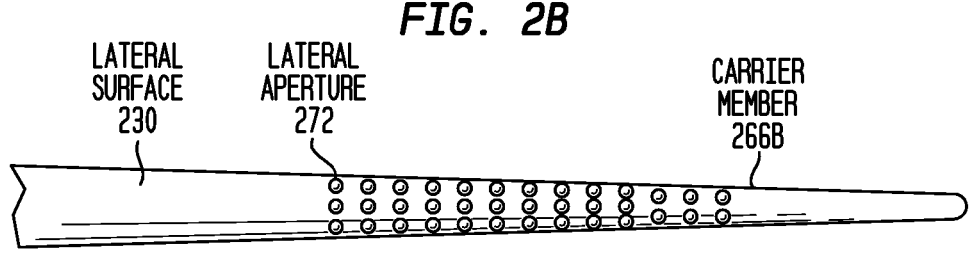
FIG. 2B is a top view of a carrier member having macro-surface features, in accordance with embodiments of the present invention.

FIG. 2B is a top view of an alternative carrier member 266B in accordance with embodiments of the present invention. In this embodiment, carrier member 266B comprises a plurality of macro-surface features in the form of apertures 272 drilled into lateral surface 230. Apertures 272 are sometimes referred to herein as lateral apertures because they extend from lateral surface 230 towards the center of carrier member 266B. That is, the opening of apertures 272 are in lateral surface 230, and the apertures have a length extending toward the center of carrier member 266A.

In certain embodiments, apertures 272 also generally each have a volume of at least 0.001 mm$^3$ and/or one or more dimensions (diameter, depth) that is at least 100 μms. In one specific embodiment, apertures 272 have a diameter of approximately 0.2 mms, while in other embodiments apertures have a diameter in the range of approximately 0.1 mms to approximately 0.4 mms.

Similar to the indentations described above with reference to FIG. 2A, apertures 272 have a configurations such that when a liquid drug is applied to carrier member 266B, a quantity of the drug will collect within the apertures, thereby at least temporarily retaining the liquid therein. In certain embodiments, capillary forces may assist in causing the liquid to enter into, and be retained in, apertures 272. Although in the embodiments of FIG. 2A the drug is retained within apertures 272, such retention is still referred to herein as being adjacent the surface of carrier member 266B.

In certain embodiments, lateral apertures 272 are drilled using a laser. In other embodiments, lateral apertures 272 are formed in the carrier member during the molding process.

As noted, in the embodiments of FIG. 2B, apertures 272 are shown on lateral surface 230 of carrier member 266B. It would be appreciated that in certain embodiments apertures 272 may be on medial surface 232 and, in such embodiments, are referred to as medial apertures. In such embodiments, the opening of apertures 272 are in medial surface 232, and the apertures have a length extending toward the center of carrier member 266B.

Figure 2C:
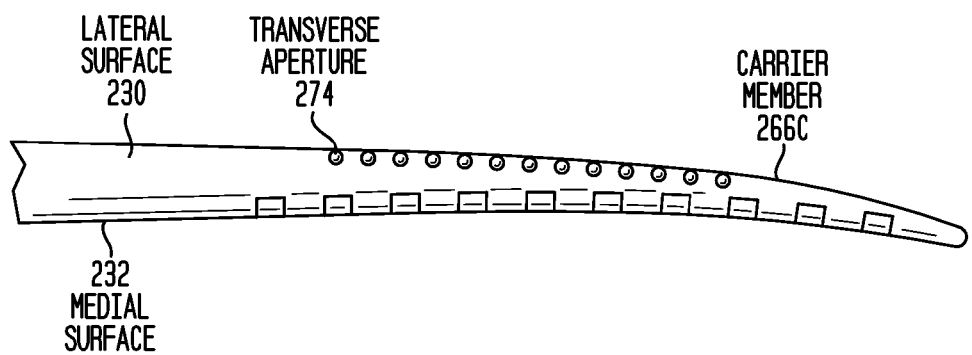
FIG. 2C is a side view of a carrier member having macro-surface features, in accordance with embodiments of the present invention.

In other embodiments, apertures may be on the surface of carrier member between the lateral and medial surfaces 230, 232. FIG. 2C is a side view of an alternative such embodiment, referred to as carrier member 266C. In this illustrative embodiment, carrier member 266C comprises a plurality of macro-surface features in the form of apertures 274 drilled or otherwise formed into carrier member 266C between lateral surface 230 and medial surface 232. Apertures 274 are sometimes referred to herein as transverse apertures because they extend at least partially through carrier member 266C in the transverse direction.

In embodiments of the present invention, apertures 274 extend varying distances across carrier member 266C. For example, apertures 274 may extend from the surface only part-way to the center of carrier member 266 or to near the center. In other embodiments, apertures 274 may extend past the center, but not to the opposing surface, while in still other embodiments apertures 274 extend through the entire carrier member.

In certain embodiments, apertures 274 also generally each have a volume of at least 0.001 mm$^3$ and/or one or more dimensions (diameter, depth) that is at least 100 μm. In one specific embodiment, apertures 274 have a diameter of approximately 0.2 mms, while in other embodiments apertures have a diameter in the range of approximately 0.1 mms to approximately 0.4 mms.

FIGS. 2B and 2C illustrate the use of apertures 272, 274 in different arrangements. It would be appreciated that the size, location and arrangement of apertures 272, 274 may vary depending on, for example, the liquid drug that will delivered, size of the carrier member, etc. In one embodiment, each aperture 272, 274 has a 0.2 mm diameter and a depth of approximately 0.5 mm. Other diameters and depths may also be used.

Similar to lateral apertures 272 of FIG. 2B, transverse apertures 274 are sized and/or shaped such that when a liquid drug is applied to carrier member 266C, a quantity of the drug will collect within the apertures. In certain embodiments, capillary forces may assist in causing the liquid to enter into, and be retained in, apertures 274.

Figure 2D:
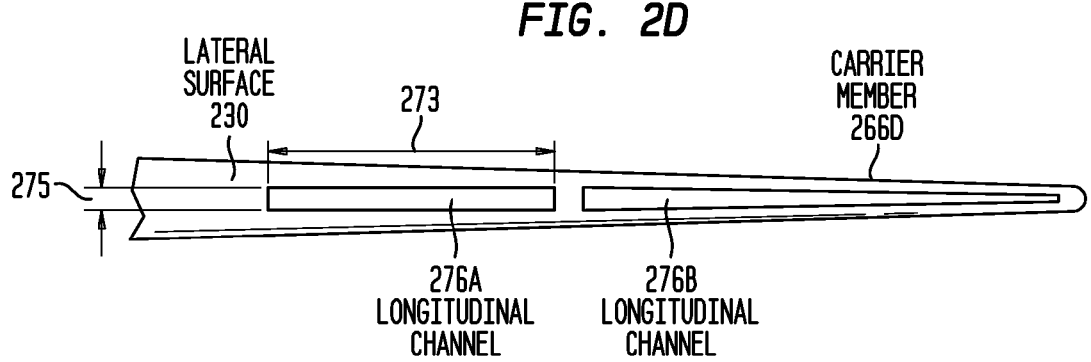
FIG. 2D is a top view of a carrier member having macro-surface features, in accordance with embodiments of the present invention.

FIG. 2D is a top view of an alternative carrier member 266D in accordance with embodiments of the present invention. In this embodiment, carrier member 266D comprises macro-surface features in the form of a plurality of longitudinally-extending channels 276. Longitudinal channels 276 are sized and/or shaped such that when a liquid drug is applied to carrier member 266D, a quantity of the drug with collect within the channels. In certain embodiments, capillary forces may assist in causing the liquid to enter into, and be retained in, channels 276.

Longitudinal channels 276 each have at least one dimension (length, width, depth) of at least 100 μm and/or a volume of at least 0.001 mm$^3$. In the embodiment of FIG. 2D, channel 276A has a width 275 of approximately 0.3 mm, a depth of approximately 0.2 mm, and a length of approximately 8 mm. It would be appreciated that FIG. 2D is not necessarily shown to scale, and that other dimensions are within the scope of the present invention. For example, channels 276 may have a length of approximately 0.1 mm up to a length that is substantially the same as the length of the carrier member.

In certain embodiments, longitudinal channels 276 are formed during molding of carrier member 266D. In other embodiments, channels 276 are formed after the molding process.

The use of the term "channels" in the embodiments of FIG. 2D is not intended to limit the shape, size or configuration of the indentations 275. For example, the use of the term "channels" does not require that the indentations 276 have a rectangular shape. In certain embodiments, the corners at the bottom of indentations 276 are rounded.

FIG. 2D illustrates a portion of carrier member 266D having two longitudinal channels formed therein, and the channels are substantially aligned with one another. It would be appreciated that channels 276 may have different shapes, sizes and arrangements depending on, for example, the liquid drug that will delivered, size of the carrier member, etc.

Channels 276 may have a number of different sizes and shapes in different embodiments of the present invention. In one embodiment, an elongate channel having a width of 0.2 mm, a depth of 0.3 mm, and a length of 10 mm is formed into the carrier member. In other embodiments, channels may be parallel with one another, overlapping, interconnected, etc.

In certain embodiments, longitudinal channels 276 are formed during molding of carrier member 266D. In other embodiments, channels 276 are formed after the molding process.

FIG. 2E is a perspective view of an alternative carrier member 266E in accordance with embodiments of the present invention. In this embodiment, carrier member 266E comprises macro-surface features in the form of a plurality of transverse channels 276 that extend across lateral surface 230. Transverse channels 278 are sized and/or shaped such that when a liquid drug is applied to carrier member 266E, a quantity of the liquid will collect within the channels. Transverse channels 278 each have least one dimension (length, width, depth) of at least 100 μm and/or a volume of at least 0.001 mm$^3$. In certain embodiments, capillary forces may assist in causing the liquid to enter into, and be retained in, channels 278.

FIG. 2E illustrates embodiments of the present invention in which channels 278 have a convex bottom that generally follows the circumferential curve of carrier member 266E. In alternative embodiments, the bottom of channels 278 are substantially planar or concave.

It would be appreciated that transverse channels 278 may have different shapes, sizes and arrangements depending on, for example, the liquid drug that will delivered, size of the carrier member, etc. In one exemplary embodiment, each transverse channel 278 has a width of 0.3 mm and a depth of 0.3 mm. In another embodiment, channels 278 have a width of approximately 0.3 mm and a depth of approximately 0.2 mm. Other dimensions are within the scope of the present invention.

In certain embodiments, transverse channels 278 are formed during molding of carrier member 266E. In other embodiments, channels 278 are formed after the molding process. FIG. 2F illustrates another embodiment of a carrier member 266F in accordance with embodiments of the present invention. In this embodiment, carrier member 266F comprises macro-surface features in the form of a plurality of generally square or rectangular indentations 279 in accordance with embodiments of the present invention. Indentations 279 are sized and/or shaped such that when a liquid drug is applied to carrier member 266F, a quantity of the liquid will collect within the indentations. Each indentation 279 has least one dimension (length, width, depth) of at least 100 μm and/or a volume of at least 0.001 mm$^3$. In certain embodiments, capillary forces may assist in causing the liquid to enter into, and be retained in, indentations 279.

It would be appreciated that indentations 279 may have different shapes, sizes and arrangements depending on, for example, the liquid drug that will delivered, size of the carrier member, etc. In one exemplary embodiment, each indentations have a width of 0.3 mm, a depth of 0.3 mm and a length of 0.3 mm. In another embodiment, indentations 279 have a width of approximately 0.3 mm, a depth of approximately 0.2 mm, and a length of 0.3 mm. Other dimensions are within the scope of the present invention.

As previously noted, macro-surface features in accordance with embodiments of the present invention may be collections of indentations in, or protrusion from, the surface of a carrier member. FIGS. 2A-2F are exemplary embodiments of carrier members having different indentations, while FIGS. 3A-5, described below, are exemplary embodiments of carrier members having different protrusions.

Figure 3A:
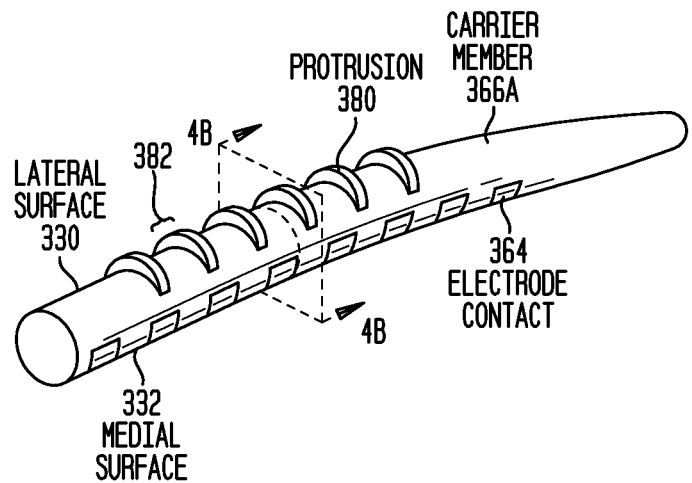
FIG. 3A is a side view of a portion of a carrier member having surface features, in accordance with embodiments of the present invention.
Figure 3B:
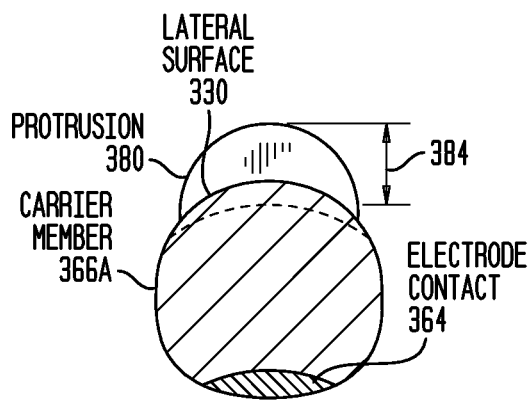
FIG. 3B is cross-sectional view of the carrier member of FIG. 3A.

FIGS. 3A and 3B are perspective and cross-sectional views, respectively, of a carrier member 366A. Similar to the embodiments described above, carrier member 366A has a lateral surface 330, medial surface 332 and a plurality of electrode contacts 364 disposed in the medial surface.

As shown, carrier member 366A further comprises a plurality of planar flexible protrusions 380 having a curved outer surface. As used herein, planar means that protrusions 380 have a substantially consistent thickness 382. Protrusions 380 have a configuration (sized, shaped or spaced) such that when a liquid drug is applied to carrier member 366A, a quantity of the drug will collect between the protrusions. As such, the drug will be, at least temporarily, retained adjacent the surface of carrier member 366A. In certain embodiments, protrusions 380 have one more dimensions that are at least 100 μm, or define a volume between adjacent protrusions that is at least 0.001 mm$^3$.

In the embodiments of FIGS. 3A and 3B, protrusions 380 are shown on lateral surface 330 of carrier member 366A. It would be appreciated that in certain embodiments protrusions 380 may be on medial surface 332, or may be on the surface of carrier member 366A between the lateral and medial surfaces 330, 332.

Figure 3C:
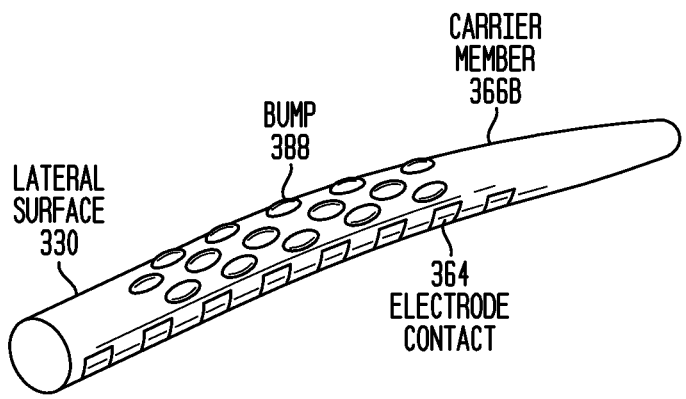
FIG. 3C is a side view of a carrier member having surface features, in accordance with embodiments of the present invention.

FIG. 3C illustrates another embodiment of the present invention in which a carrier member 366B has a plurality of protrusions in the form of bumps or mounds 388 formed on lateral surface 330 is shown in FIG. 3C. Bumps 388 extend from surface 330 and have a configuration such that when a liquid drug is applied to carrier member 366B, a quantity of the drug will collect between the bumps. As such, the drug will be, at least temporarily, retained adjacent the surface of carrier member 366B. In certain embodiments, bumps 388 have one more dimensions that are at least 100 μm, or define a volume between adjacent protrusions that is at least 0.001 mm$^3$.

In the embodiments of FIG. 3C, bumps 388 are shown on lateral surface 330 of carrier member 366B. It would be appreciated that in certain embodiments bumps 388 may be on medial surface 332, or may be on the surface of carrier member 366B between the lateral and medial surfaces 330, 332.

In certain embodiments of the present invention, the protrusions in are substantially flexible and do not provide structural support to the carrier member. That is, the protrusions are configured so that they do no affect operation of electrodes 364 once in situ. In other embodiments, the protrusions do provide structural support to the carrier member and enhance the operation of the carrier member. In such embodiment, the protrusions are substantially rigid and are designed to assist in proper positioning of the carrier member in the recipient.

Figure 4A:
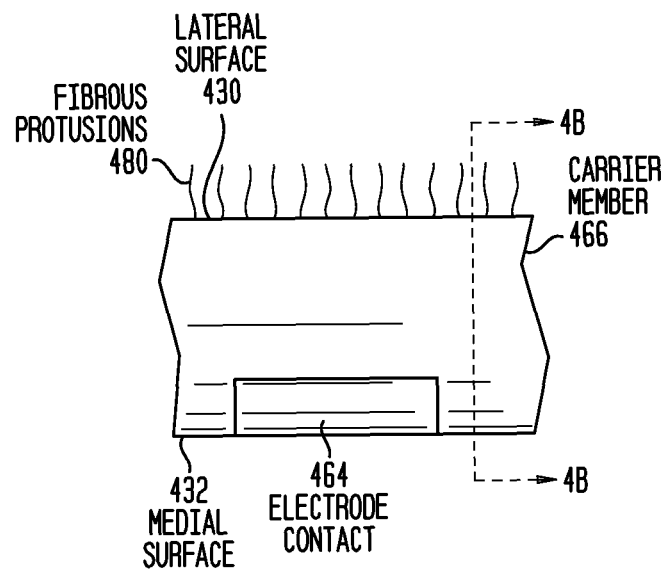
FIG. 4A is a side view of a segment of a carrier member having surface features, in accordance with embodiments of the present invention.
Figure 4B:
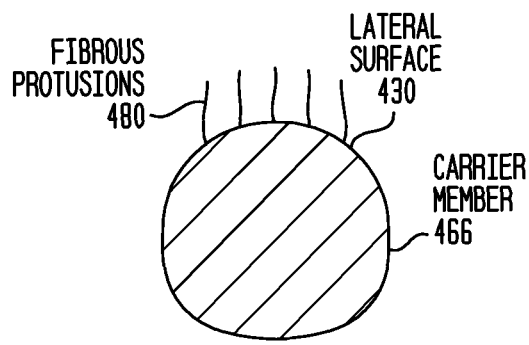
FIG. 4B is a cross-sectional view of the carrier member of FIG. 4A.

FIGS. 4A and 4B are perspective and cross-sectional views, respectively, of a section of a carrier member 466. Similar to the embodiments described above, carrier member 466 has a lateral surface 430, medial surface 432 and a plurality of electrode contacts 464 disposed in the medial surface.

As shown, carrier member 466 further comprises a plurality of fibrous protrusions 480 that are sized, shaped or spaced such that when a liquid drug is applied to carrier member 466, a quantity of the drug will collect between the protrusions. As such, the drug will be, at least temporarily, retained adjacent the surface of carrier member 466. In embodiments of the present invention, fibrous protrusions 480 are hair-like elements that are substantially flexible. In certain embodiments, fibrous protrusions 480 have dimensions (lengths, diameters and/or widths) that are at least approximately 100 μm, or define a volume between adjacent protrusions that is at least 0.001 mm$^3$. In other embodiments, protrusions 480 are macroscopic in size and have dimensions that are substantially smaller 100 μm. In certain such embodiments, the dimensions of protrusions 480 are a few μms, or smaller.

In the embodiments of FIGS. 4A and 4B, fibrous protrusions 480 are shown on lateral surface 430 of carrier member 466. It would be appreciated that in certain embodiments fibrous protrusions 480 may be on medial surface 432, or may be on the surface of carrier member 466 between the lateral and medial surfaces 430, 432.

Additionally, FIGS. 4A and 4B illustrate embodiments in which fibrous protrusions 480 are used without any additional surface features. However, it would be appreciated that, in alternative embodiments, fibrous protrusions 480 may be used with other surface features to increase the retention of a liquid drug. For example, in one embodiment, fibrous protrusions 480 may be disposed in an indentation, such as indentations 270, 272, 274, 276, 278 or 279 described above, or any other indentation. In another example, fibrous protrusions 480 are disposed on or between protrusions 380, 388 described above, or any other protrusions.

As noted above, carrier members in accordance with embodiments of the present invention are generally formed from a biocompatible polymer, such as silicone. Protrusions in accordance with embodiments of the present invention may be, in certain embodiments, formed from the same material as the carrier member. In such embodiments, the protrusions may be unitary with carrier member. That is, the protrusions are formed together during, for example, molding of the carrier member. In other embodiments, the protrusions are separate components that are attached to the carrier member at a later point in time.

In embodiments of the present invention, the protrusions and/or indentations are made from, or include a layer of, a material that is different from the material used for the main body of the carrier member. In such embodiments, the protrusions or indentations may be integrated into the carrier member during, for example, molding, or attached at a later point in time.

Silicone and other polymer materials used for carrier members generally have a low wettability that does not readily allow for retention of liquid. As such, in certain embodiments, protrusions or indentations are formed from a different material, or surface modified silicone, that facilitates the adhesion of the liquid thereto. The use of a different material having a higher wettability than silicone increases the volume of fluid retained over the embodiments that use the same material for the protrusions as for the main body of the carrier member.

In certain embodiments, protrusions and/or indentations are formed from a bio-resorbable material. In such embodiments, the protrusions or indentations provide additional surface for area for retention of the liquid drug during, and immediately following implantation. However, after the drug is dispersed, the bio-resorbable material resorbs so only a conventional carrier member remains.

Figure 5:
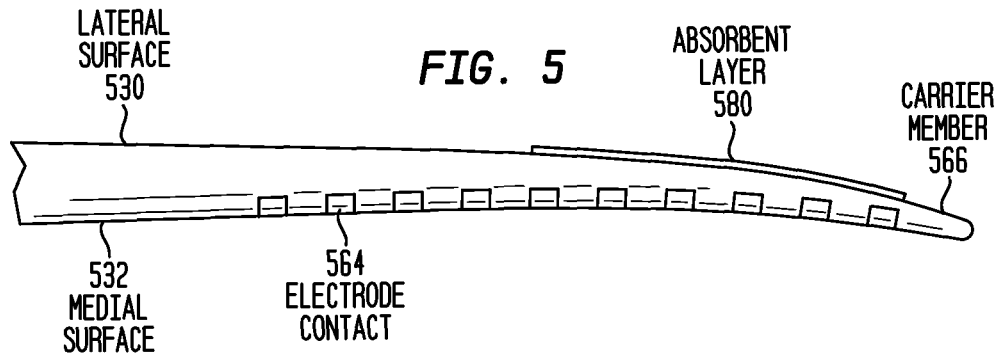
FIG. 5 is a side view of a carrier member having surface features, in accordance with embodiments of the present invention.

FIG. 5 is a side view of another carrier member 566 in accordance with embodiments of the present invention. Similar to the embodiments described above, carrier member 566 has a lateral surface 530, medial surface 532 and a plurality of electrode contacts 564 disposed in the medial surface.

As shown, carrier member 566 further comprises a surface feature in the form of an absorbent layer 580 attached to lateral surface 530. When a liquid drug is applied to carrier member 566, absorbent layer 580 will absorb and retain the liquid. Absorbent layer 580 may comprise, for example, a sponge layer.

In the embodiments of FIG. 5B, absorbent layer 580 is shown on lateral surface 530 of carrier member 566. It would be appreciated that in certain embodiments absorbent layer 580 may be on medial surface 532, or may be on the surface of carrier member 566 between the lateral and medial surfaces 530, 532.

Additionally, FIG. 5 illustrate embodiments in which absorbent layer 580 is used without any additional surface features. However, it would be appreciated that, in alternative embodiments, absorbent layer 580 may be used with other surface features to increase the retention of a liquid drug. For example, in one embodiment, absorbent layer 580 may be disposed in an indentation, such as indentations 270, 272, 274, 276, 278 or 279 described above, or any other indentation. In another example, absorbent layer 580 may be disposed on or between protrusions 380, 388 described above, or any other protrusions.

Figure 6:
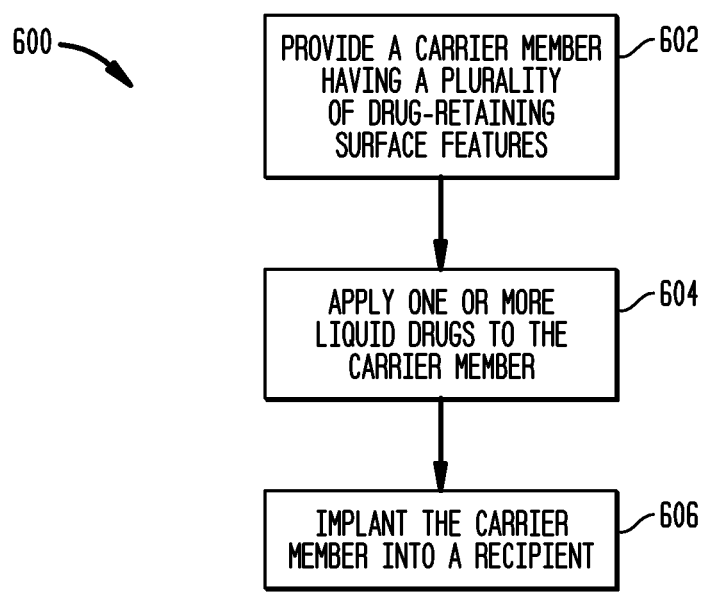
FIG. 6 is a flowchart illustrating use of a carrier member, in accordance with embodiments of the present invention.

FIG. 6 is a flowchart of a method 600 for use of a carrier member, in accordance with embodiments of the present invention. Method 600 begins at step 602 where a carrier member having a plurality of liquid-retaining surface features is provided. At step 604, one or more liquid drugs are applied to the carrier member, and at step 606, the carrier member is implanted in a recipient.

As noted at step 602 of FIG. 6, at least one, and optionally a plurality of drugs are applied to the carrier member. The liquid drug may be applied through a number of different processes. For example, the carrier member may be dipped into the liquid drug, the drug poured over the carrier member, the drug may be sprayed onto the carrier member, etc. In one specific drug application example, the distal end of carrier member is dipped into a first liquid drug until the entire length of the carrier member is immersed. That is, the distal end to the proximal end is immersed in the drug. The carrier member is then removed from the first drug. The first drug may be allowed to dry or solidify, or the carrier member is directly dipped into a second liquid drug. As would be appreciated, the carrier member may be dipped into the second liquid drug from different ends, or to different depths so that the drugs are applied to different portions of the carrier member. In one exemplary arrangement, only the distal end (tip) of the carrier member is inserted into the second drug, resulting in a double coating of drugs only on the distal end of the carrier member. In another arrangement, the substantial entirety of the carrier member is dipped into the second drug.

In another method for application of a plurality of drugs to the carrier member, the distal end of the carrier member is dipped into a first liquid drug until the entire length of the carrier member is immersed. The carrier member is then removed from the first drug, and a portion of the carrier member is dipped into a solution that removes the first drug from that section. The section from which the first drug has been removed can then be dipped into a second drug. This results in a carrier member having different drugs only on different sections of the carrier member. As would be appreciated, the carrier member may be dipped into the removal solution and the second drug from different ends, or to different depths so that the different drugs are applied different portions of the carrier member. In one exemplary arrangement, only the distal end (tip) of the carrier member is inserted into the removal solution and the second drug. In another arrangement, the entire carrier member is substantially is dipped into the removal solution and the second drug.

As noted above, the configuration (type, size and/or shape) of a surface feature may be selected based, at least in part, on the drug that is to be retained therein. This is a result of the material properties of the drug, and that surface features having certain configurations will better retain certain drugs. As such, in another method for application of a plurality of drugs to the carrier member, the carrier member has surface features groups or arrangements each with two different configurations. One arrangement is of a type, size and/or shape that facilitates retention of a first drug, while the other arrangement of surface features is of a type, size and/or shape that facilitates retention of a second drug. In this embodiment, the carrier member is dipped into the first drug, and the first drug is retained in the first arrangement of surface features. The carrier member is then dipped in the second drug, and the second drug is retained in the second arrangement of surface features.

It would be appreciated that the first and second surface arrangements may be disposed at various locations on the carrier member. In one embodiment, the second arrangement is only on the distal end of the carrier member.

Embodiments of the present invention have been primarily described above with reference to a carrier member arrangement that temporarily retains drugs adjacent the surface of the carrier member. As such, upon implantation of the carrier member, the drugs are immediately delivered to the body. Certain embodiments of the present invention are directed to a longer term drug delivery configuration.

In one longer-term embodiment, the carrier member is coated with a drug release impeding material that slows down the release of the drugs into the body. In one specific such embodiment, the liquid drug is mixed with an ultraviolet (UV) stabilized silicone. In such embodiments, the drug/silicone mixture is applied to the carrier member such that the mixture is retained in the surface features. Subsequently, the mixture is cured under a UV light.

In further embodiments, the new immediate drug delivery is used in combination with longer-term drug delivery. In one such embodiment the carrier member has drug-retaining surface features for immediate drug delivery, and the carrier member body is impregnated with a drug for long term delivery. In such embodiments, the drug is integrated into the polymeric coating of the carrier member, and the drugs are releases over a period of time following the immediate drug delivery via the surface features.

In another embodiment, the carrier member has drug-retaining surface features for immediate drug delivery, and the carrier member has, or is coupled to, a reservoir for long term delivery. In such embodiments, the carrier member further includes drug-delivery ports that releases the drugs into the patient. The reservoir may be, for example, within the carrier member, or may be fluidically coupled to a lumen within the carrier member.

In a still other embodiment, the carrier member has drug-retaining surface features for immediate drug delivery, and an independently-manufactured drug delivery capsule carrying a drug. In such embodiments, the drug delivery capsule may be joined with the carrier member subsequent to the device's manufacture and/or sterilization, and prior to, concurrently with, or subsequent to the implantation of the carrier.

The above are examples of combinations of the immediate drug delivery with longer-term drug delivery solutions. It would be appreciated that these examples are merely illustrative, and do not limit the present invention. In particular, it would be appreciated that embodiments of the present invention may be used with any longer-term drug delivery solution now know or later developed.

As previously noted, for ease of description, embodiments of the present invention have been primarily described herein with reference to surface features in or on an intra-cochlear portion of a cochlear implantable elongate carrier member. However, it would be appreciated that the drug-retaining surface features of the present invention may be implemented in a variety of implantable components. For example, with reference to FIG. 1B, surface features may be disposed adjacent the surface of receiver unit 134, stimulator 132, or on other portions of stimulating assembly 150. As such, drug-retaining surface features may be disposed anywhere in or on extra-cochlear region 152 or lead region 158. In certain such embodiments, the components include a polymeric surface, and the surfaces features are disposed at this surface.

Furthermore, the surface features may be provided at different locations within intra-cochlear region 160. As such, surface features may be positioned only at the distal end of carrier member 166, adjacent the cochleostomy, etc.

In certain embodiments of the present invention, the receiver and stimulator are contained in an implantable component referred to herein as the stimulator/receiver unit. FIGS. 7A-8B are exemplary embodiments of receiver/stimulator units having surface features in accordance with embodiments of the present invention.

Figure 7A:
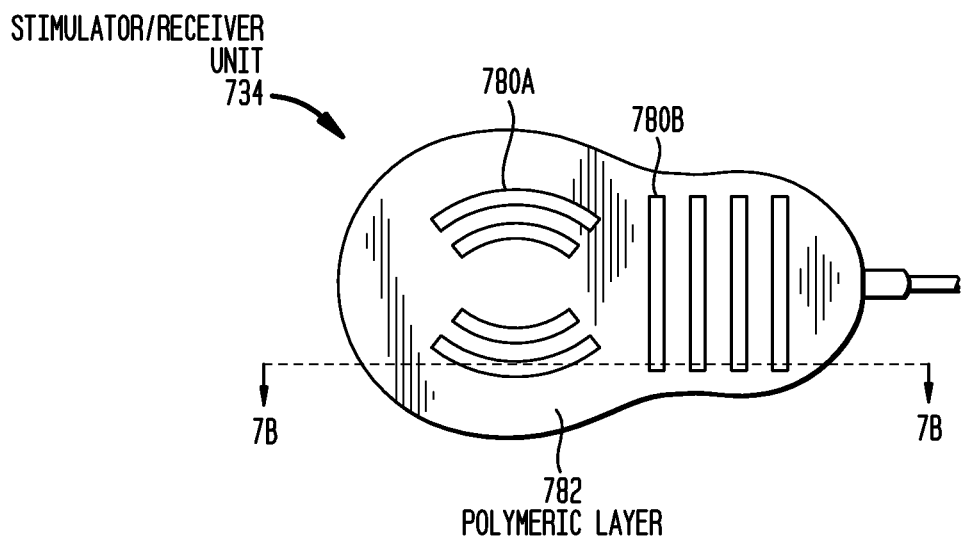
FIG. 7A is a top view of an implantable component having surface features, in accordance with embodiments of the present invention.
Figure 7B:
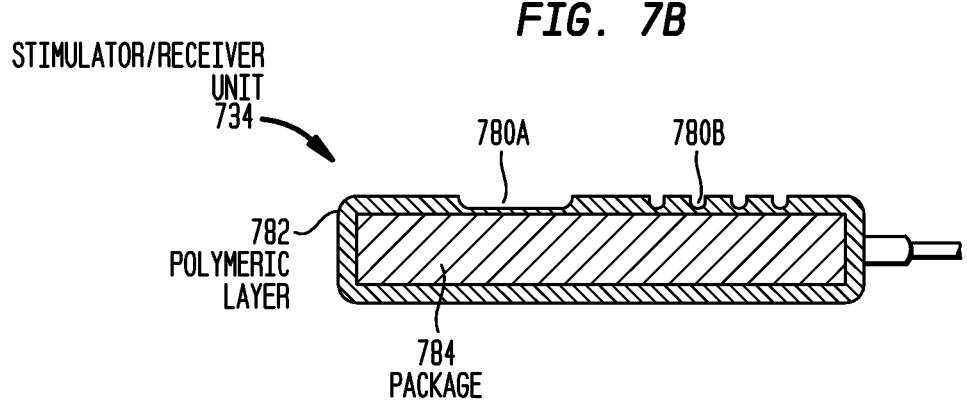
FIG. 7B is a cross-sectional view of the implantable component of FIG. 7A.

In the embodiments of FIGS. 7A and 7B, stimulator/receiver unit 734 comprises a package 784 that contains the functional components. Enclosing package 784 is a polymeric layer 782. Layer 782 may be a coating of polymeric material that is applied to package 784, or may simply be an outer polymeric surface of package 782. For ease of illustration, layer 782 is shown as a separate layer.

Disposed in layer 782 is a plurality of indentations 780. Specifically, indentations 780A are curved channels having a general arched shape, while indentations 780B are substantially straight channels.

The use of the term "channels" in embodiments of the present invention not intended to limit the shape, size or configuration of the indentations 780. For example, the use of the term "channels" does not require that the indentations 780 have a rectangular shape, or a square cross-sectional. In the embodiments of FIGS. 7A and 7B, the corners at the bottom of indentations 780 are rounded to provide a substantially smooth surface. Additionally, in specific embodiments of the present invention, an indentation 780 preferably has a width that is greater than its depth.

It would be appreciated that the indentations shown in FIGS. 7A and 7B are merely illustrative and that other types of indentations may also be disposed in layer 782. For example, indentations 270, 272, 274, 276, or 278 described above may be also be disposed in layer 782.

Figure 8A:
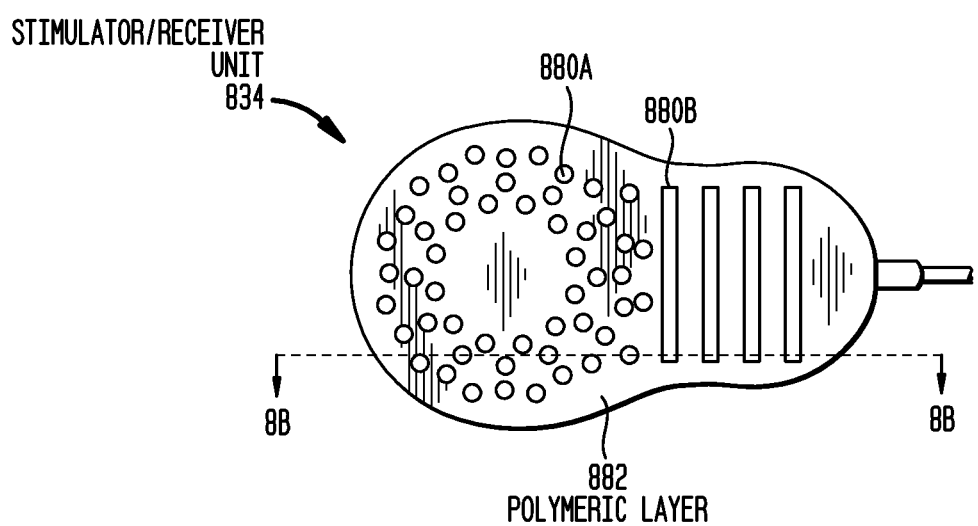
FIG. 8A is a top view of an implantable component having surface features, in accordance with embodiments of the present invention.
Figure 8B:
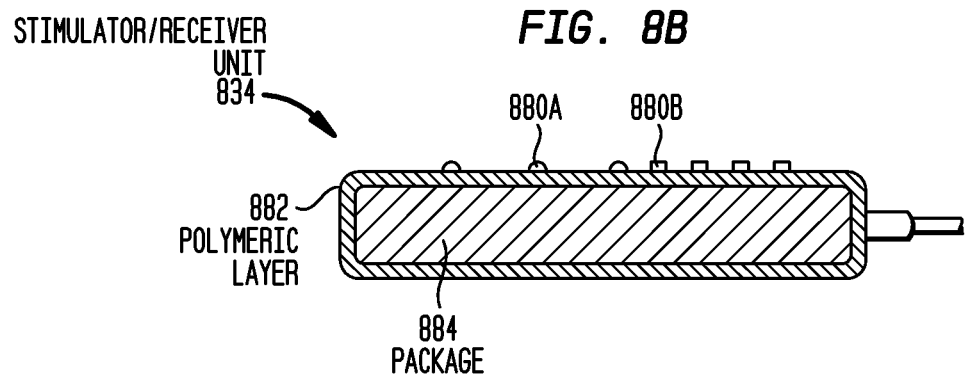
FIG. 8B is a cross-sectional view of the implantable component of FIG. 8A.

In the embodiments of FIGS. 8A and 8B, stimulator/receiver unit 834 comprises a package 884 that contains the functional components. Enclosing package 884 is a polymeric layer 882. Similar to the above embodiments of FIGS. 7A and 7B, layer 882 may be a coating of polymeric material that is applied to package 884, or may simply be an outer polymeric surface of package 882. For ease of illustration, layer 882 is shown as a separate layer.

Disposed in layer 882 is a plurality of protrusions 880. Specifically, protrusions 880A are bumps, while indentations 880B are substantially straight members. It would be appreciated that the protrusions shown in FIGS. 8A and 8B are merely illustrative and that other types of protrusions may also be disposed at layer 882. For example, protrusions 380, 388, 480, or 580 described above may be also be disposed at layer 882.

Additionally, it would be appreciated that the embodiments of the present invention are not mutually exclusive, and that the embodiments may be combined with one another as desired. For example, implantable components in accordance with embodiments of the present invention may include any combination of protrusions and indentations for retention of liquid drug(s).

While various embodiments have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive. Additionally, it will be appreciated that any features, components, elements, etc., described above in relation to different exemplary embodiments may be implemented together.

What is claimed is:

1. An implantable stimulating assembly, comprising:
   a carrier member configured to be implanted in a recipient;
   a plurality of electrode contacts disposed in the surface of the carrier member; and
   one or more macro-surface features disposed in the surface of the carrier member, wherein the macro-surface features are:
   disposed in the surface of the carrier member adjacent to the electrode contacts;
   and dimensioned such that they are, following application of a liquid drug, configured to retain a quantity of the liquid drug adjacent to the surface of the carrier member.

2. The assembly of claim 1, wherein the macro-surface features are indentations in the surface of the carrier member.

3. The assembly of claim 2, wherein the indentations are apertures in the carrier member.

4. The assembly of claim 2, wherein the macro-surface features are longitudinal channels in the carrier member.

5. The assembly of claim 2, wherein the macro-surface features are transverse channels in the carrier member.

6. The assembly of claim 1, wherein the plurality of macro-surface features are protrusions at the surface of the carrier member.

7. The assembly of claim 6, wherein the protrusions are substantially planar protrusions having a curved outer surface.

8. The assembly of claim 6, wherein the protrusions are bumps extending from the carrier member surface.

9. The assembly of claim 6, wherein the carrier member is a first material, and wherein the protrusions are a second material.

10. The assembly of claim 1, wherein the one or more macro-surface features comprise an absorbent layer attached to the carrier member surface.

11. The assembly of claim 1, wherein the elongate implantable stimulating assembly is connected to a stimulator/receiver unit of a cochlear implant.

12. The assembly of claim 1, wherein the macro-surface features and electrode contacts are disposed such that the macro-surface features are interspersed in the surface of the carrier member.

13. The assembly of claim 1, wherein the macro-surface features are disposed in a first portion of the surface of the carrier member and the electrode contacts are disposed in a second portion the surface of the carrier member, wherein the first portion and second portion overlap.

14. The assembly of claim 1, wherein the macro-surface features are disposed in a first portion of the surface of the carrier member and the electrode contacts are disposed in a second portion the surface of the carrier member, wherein the first portion and second portion do not overlap.

15. A method of delivering drugs to a recipient using an elongate implantable stimulating assembly, wherein the stimulating assembly comprises a carrier member configured to be implanted in a recipient, a plurality of electrode contacts disposed in the surface of the carrier member, and one or more macro-surface features disposed in the surface of the carrier member, wherein the macro-surface features are:
   disposed in the surface of the carrier member adjacent to the electrode contacts; and
   dimensioned such that they are, following application of a liquid drug, configured to retain a quantity of the liquid drug adjacent to the surface of the carrier member, the method comprising:
   applying one or more liquid drugs to the component; and
   implanting the implantable component into the recipient.

16. The method of claim 15, wherein applying the one or more liquid drugs to the carrier member comprises:
   dipping a first length of the carrier member into a first liquid drug; and
   dipping a second length of the carrier member into a second liquid drug.

17. The method of claim 15, wherein the first length of the carrier member is different than the second length of the carrier member.

18. The method of claim 15, wherein the first length of the carrier member is the same as the second length of the carrier member.

19. The method of claim 15, wherein applying the one or more liquid drugs to the carrier member comprises:
   dipping a first length of the carrier member into a first liquid drug;
   dipping a first portion of the first length of the carrier member into a removal solution so as to remove the first drug from the first portion;
   dipping the first portion of the first length of the carrier member into a second liquid drug; and
   coating the carrier member with a drug release impeding material.

20. An implantable component of a medical device, comprising:
   a polymeric surface;
   a plurality of electrode contacts disposed in the polymeric surface; and
   one or more macro-surface features disposed in the polymeric surface, wherein each macro-surface feature is disposed in a different surface area of the polymeric surface than each of the electrode contacts, and
   wherein the macro-surface features are dimensioned such that they are, following application of a liquid drug, configured to retain a quantity of the liquid drug adjacent to the polymeric surface.

* * * * *